United States Patent [19]

Neubeck

[11] 4,233,405

[45] Nov. 11, 1980

[54] PROCESS FOR SPRAY DRYING ENZYMES

[75] Inventor: Clifford E. Neubeck, Hatboro, Pa.

[73] Assignee: Rohm and Haas Company, Philadelphia, Pa.

[21] Appl. No.: 83,449

[22] Filed: Oct. 10, 1979

[51] Int. Cl.$^3$ ............................................. C12N 9/98
[52] U.S. Cl. .................................. 435/187; 435/203; 435/222
[58] Field of Search .................. 435/187, 203, 222

[56] References Cited

U.S. PATENT DOCUMENTS 4,180,917   1/1980   Neubeck ................................. 34/5

FOREIGN PATENT DOCUMENTS 40-17169   2/1979   Japan .

OTHER PUBLICATIONS

Chemical Abstracts 76, 32816f (1972).
Chemical Abstracts 81, 62097t (1974).

*Primary Examiner*—Lionel M. Shapiro

[57] ABSTRACT

This invention involves a process for the preparation of spray dried enzymes.

10 Claims, No Drawings

PROCESS FOR SPRAY DRYING ENZYMES

BACKGROUND OF THE INVENTION

The concept of using spray drying for preparing dry enzyme compositions is known in the art. A protease unhairing enzyme in the form of a whole crude culture of bacteria (*Pseudomonas effusa*) has been successfully spray dried. A crude culture of *Bacillus subtilis* to which wood flour was added has also been spray dried. The stability of the activity was poor in the latter case and together with the lack of any cost advantage made spray drying over tray drying impractical. A protease (Bacillus spp.) was spray dried using ultrafilter concentrates but odor, high bacteria count, and hazards related to inhalation of alkaline protease dust made this method of manufacture impractical.

Subsequently attempts were made to develop a process for spray drying enzyme concentrates (primarily from surface culture) obtained by ultrafilter concentration of several culture filtrates. These trials indicated that spray drying of enzymes was possible but activity yields and solids recovery were frequently low, a large amount of product collected on the chamber walls, moisture in the final product was very high, caking and darkening of the dried concentrate was frequently observed and activity retention was poor during storage at room temperature.

Freeze drying has also been utilized to obtain a dry enzyme composition. Initially, freeze drying gave better yields than spray drying. Several of the concentrates still gave problems with freeze drying until it was noted that supplementation of the enzyme concentrates with selected combinations of inorganic salts and insoluble ingredients gave improved results. These findings became the basis of U.S. application Ser. No. 939,745 filed Sept. 9, 1978 by Clifford E. Neubeck assigned to a common assignee U.S. Pat. No. 4,180,917, issued Jan. 1, 1980.

In initial studies, several different formulations of enzyme concentrates were tested in an attempt to select the type and composition of additives to be used in spray drying. These experiments, involved in vacuo drying of bacterial alpha-amylase concentrate to which various salts and insoluble ingredients were added, demonstrated the critical nature of the additives. The variation of the additives had a significant effect on the physical nature, activity recovery, moisture level, lumping, color, etc., of the product. As a result of the above experimentation, initial spray drying experiments were conducted.

SUMMARY OF THE INVENTION

This invention relates to a process for spray drying enzymes which comprises concentrating a liquid enzyme solution by ultrafiltration, adding to said concentrate water-insoluble salts, optionally in the presence of water-insoluble suspenders and thickeners, intimately mixing the concentrate composition, and spray-drying said concentrate composition at air inlet temperatures of from about 120° C. to about 180° C., and air outlet temperatures from about 68° C. to about 85° C.

In accordance with the process of this invention any conventional ultrafiltration equipment can be utilized as long as it fills the requirements of being able to not only concentrate the liquid enzyme solution but also remove low molecular weight sugars, amino acids, and peptides which are the major cause of discoloration, hygroscopicity, odor, gumming, caking and other similar factors which lead to deterioration of the product and in some cases to unmarketable products.

Water insoluble salts that can be utilized in the process of this invention include tribasic calcium phosphate, tribasic magnesium phosphate, calcium carbonate, calcium hypophosphate, calcium magnesium silicate, calcium silicate, calcium sulfite, calcium tartarate, magnesium oxide and magnesium silicate and the like. Any water soluble salts which when combined form water insoluble salts can also be utilized. By water soluble salt it is meant any salt which is at least slightly soluble in the media in which it is to be dissolved.

Water insoluble suspenders and thickeners which may optionally be employed in the process of this invention include cornstarch, potatoe starch, tapioca, cellulose and the like.

In accordance with the process of this invention the air inlet temperatures which can be utilized for the addition of the liquid enzymes concentrate composition are from about 120° C. to about 180° C. However, a preferred temperature range for the air inlet temperature is from about 150° C. to about 177° C. more preferably from about 155° C. to about 165° C. The air outlet temperatures which can be utilized in the process of this invention for the spray dried enzyme compositions obtained by this process are from about 65° C. to about 90° C. However, a preferred temperature range for the air outlet temperature is from about 70° C. to about 85° C. more preferably from about 75° C. to about 83° C.

A preferred process of this invention relates to the preparation of a spray dried enzyme composition which comprises concentrating a liquid enzyme solution obtained from a submerged culture of an enzyme selected from Bacillus sps protease, Aspergillus sps protease or Bacillus sps amylase, by ultrafiltration, forming water insoluble salts in situ by the reaction of a water soluble phosphate salt and a water soluble calcium salt, intimately mixing the concentrate composition and spray drying the concentrate composition at air inlet temperatures from about 155° C. to about 175° C. and air outlet temperatures from about 75° C. to about 83° C.

DETAILED DESCRIPTION OF THE INVENTION

Table I gives a summary of eleven test runs made in small scale using an *Aspergillus oryzae* protease without any additives to illustrate the type of result obtained. Similar data were also obtained on other *Aspergillus oryzae* proteases.

TABLE 1

| Summary of Preliminary Spray Drying Study using *Aspergillus oryzae* protease Concentrates Without Additives[1] | | | | | | | | | | | |
|---|---|---|---|---|---|---|---|---|---|---|---|
| Test Number | 1 | 2 | 3 | 4 | 5 | 6 | 7 | 8 | 9 | 10 | 11 |
| Starting Material Activity(HU)[2] | 17100 | 17100 | 16400 | 16400 | 17100 | 17100 | 17100 | 36000 | 36000 | 47000 | 47000 |
| % Solids | 12.5 | 12.5 | 12.5 | 12.5 | 12.0 | 12.0 | 12.0 | 16.0 | 16.0 | 17.2 | 17.2 |
| Drying Conditions | | | | | | | | | | | |

TABLE 1-continued

Summary of Preliminary Spray Drying Study using *Aspergillus oryzae* protease Concentrates Without Additives[1]

| Test Number | 1 | 2 | 3 | 4 | 5 | 6 | 7 | 8 | 9 | 10 | 11 |
|---|---|---|---|---|---|---|---|---|---|---|---|
| Air T in °C. | 160 | 160 | 130 | 120 | 149 | 149 | 121 | 120 | 130 | 120 | 130 |
| Air T out °C. | 75 | 75 | 70 | 70 | 71 | 82 | 68 | 70 | 70 | 70 | 70 |
| Product activity HU[2] | 73000 | 113000 | 122000 | 125000 | 117000 | 108000 | 137000 | 184000 | 193100 | 216000 | 206000 |
| % Moisture | 13.5 | 14.1 | 10.1 | 11.3 | 11.3 | 11.5 | 12.3 | 9.4 | 9.4 | 9.4 | 10.1 |
| % Weight Recovered[3] | 16.4 | 29.8 | 49.2 | 62.8 | 41.6 | 51.0 | 57.2 | 77.1 | 78.2 | 70.7 | 66.1 |
| % Activity Recovered | 8.8 | 27.3 | 45.5 | 60.7 | 38.5 | 40.0 | 57.6 | 65.0 | 72.5 | 54.9 | 51.0 |

[1]Most of these spray dried products were gummy, dark in color and hygroscopic.
[2]An enzyme has an activity of 1000 HU per g. if 11.18 mg. of it produces an increase in soluble nitrogen of 5.0 mg. from 0.417 g. hemoglobin in 5 hours at 40° C. and pH 4.7.
[3]% Weight recovery of solids = $\frac{\text{weight out} \times \% \text{ solids}}{\text{weight in} \times \% \text{ solids}}$ 100. Solids recovery includes solids in product collected plus product in chamber plus chamber dustings.

Spray Drying Studies With Additives

The relatively poor experience with spray drying as summarized in Table I (for *Aspergillus oryzae* protease) led to the testing of a number of additives as supplements to the enzyme concentrate utilizing in vacuo drying in order to determine the effect on the physical properties of the final product. This experimentation was done on Bacterial alpha-amylase Concentrate since it was the material considered for initial testing with various additives.

Table II summarizes these results. Surprisingly the best mixture of additives from the standpoint of physical appearance (#17) did not give an exceptional yield of activity. The formation of calcium phosphate in the concentrate by mixing ammonium phosphate and lime gave distinctly better properties than adding calcium phosphate alone (#18) with starch (#14 and #19) or with ammonium phosphate, lime, and starch (#15). Starch alone was not effective. The results suggested that the manner of adding substances and the composition had a profound effect on the physical nature of the product.

Spray drying tests were made on Bacterial alpha-amylase concentrate using the concentrate alone, concentrate plus cornstarch (5%) and tricalcium phosphate (7%) added sequentially and finally a third mixture containing concentrate plus cornstarch (5%) and a dry mixture of ammonium phosphate (7%) and lime (3.6%). The dry mixture of ammonium phosphate and lime was added to the concentrate after the starch has been thoroughly suspended.

In Table II, aliquots of the enzyme Concentrate at 16% solids and 41000 FM Activity were mixed with various additives and then dried in vacuo at 45° C. The dried material was examined for texture, color, and activity in cases where the physical nature of the dried material was good. An enzyme with 1,000 starch liquifying units (FM) per g. reduced the viscosity of 300 times its weight of potato starch by 90% in 10 minutes at 70° C. and pH 6.7.

TABLE II

Laboratory Drying Experiments on Bacterial alpha-amylase Concentrate

| | Materials Added to Concentrate | | | | Appearance of Dried Product | | | | |
|---|---|---|---|---|---|---|---|---|---|
| Test Number | % NH4H2PO4 | % CaO | % Ca3(PO4)2 | % Starch | Color | Stickiness | Grinding | Activity | Activity Recovery |
| 12 | — | — | — | — | Dark | Gummy | Very Difficult | | |
| 13 | — | — | — | 10 | Dark | Gummy | Very Difficult | | |
| 14 | — | — | 14 | 10 | Light | None | Hard | 102000 | 91.3 |
| 15 | 5.2 | 3.6 | 7.0 | 10 | Dark | Slightly Gummy | Difficult | | |
| 16 | 2.6 | 1.8 | 10.8 | 10 | Light | None | Hard | 69600 | 108 |
| 17 | 10.4 | 7.2 | — | 10 | Very Light | None | Soft | 37500 | 65 |
| 18 | — | — | 14.0 | — | Light | Sl. Gummy | Hard | | |
| 19 | — | — | 10.0 | 14 | Dark | None | Hard | | |

Table III summarizes the results obtained when the various mixtures disclosed therein were spray dried.

Bacterial alpha-amylase Ultrafilter Concentrate at 25050 FM (diastase activity) and 8.0% soluble solids was divided into 3 parts:
Mix 1. No additives
Mix 2. Plus 5% cornstarch and 7% tricalcium phosphate
Mix 3. Plus 5% cornstarch, 7% NH4H2PO4 and 3.6% CaO. (Ammonium phosphate and lime mixed dry before addition to the concentrate containing starch)

Each of the compositions was then spray dried at 16,600–18,700 RPM wheel speed for atomization and air temperatures of 310° F. (154° C.) inlet and 175° F. (80° C.) outlet. Mix 1 was also dried at other combinations of wheel speed and temperature.

As noted in Table III, spray dried product prepared from Mix 1 (i.e. no additives) gave poor solids recovery and caking of the product was observed after storage for several days. Change in atomizer speed or drying temperatures did not alter the results significantly for Mix 1. Best recovery of activity and best appearance was obtained with Mix 3 but Mix 2 was more readily handled in the pumping system to the atomizer. Mix 3 gave a lower specific activity.

TABLE III

Spray Dry Test Runs With Bacterial alpha-amylase Concentrate

| Composition Dried | Wheel Speed RPM | Air Temp. °F. In | Air Temp. °F. Out | Dry Product Quality | Dry Product Activity (FM)[1] | Recovery Solids | Recovery Activity |
|---|---|---|---|---|---|---|---|
| Mix 1 | 12,000 | 310 | 173 | Poor Drying | | Poor recovery | |
| Mix 1 | 13,300 | 310 | 175 | Still Wet | 287,000 | 42.3 | 40.8 |
| Mix 1 | 16,600 | 310 | 175 | Some Caking[2] | 303,500 | 62 | 60.3 |
| Mix 1 | 16,600 | 330 | 177 | Some Caking[2] | 292,500 | 62 | 58.1 |
| Mix 1 | 16,600 | 340 | 179 | Some Caking[2] | 294,000 | 62 | 58.4 |
| Mix 1 | 16,600 | 350 | 180 | Some Caking[2] | 291,000 | 62 | 57.8 |
| Mix 2 | 18,700 | 310 | 175 | Smooth flowing Light Color | 130,000 | 87 | 80 |
| Mix 3[3] | 18,700 | 310 | 180 | Very good Light color | 102,000 | 100 | 100 |

[1] An enzyme with 1,000 starch liquifying units per g. reduces the viscosity of 300 times its weight of potato starch by 90% in 10 minutes at 70° C. and pH 6.7.
[2] Samples prepared from Mix 1 caked into a lump of material with dark color after storage.
[3] Mix 3 had a tendency to clog the nozzles of wheel atomizer.

Large scale runs were made with Bacterial alpha-amylase Concentrate in two different size driers. Basically the additive composition of Mix 2 (Table III) was used but slightly different ratios of starch to calcium phosphate were employed and the ultrafiltration concentration was slightly more efficient in the larger run so that a larger amount of low molecular weight soluble solids were removed. Example 1 gives the details of the smaller run while Example 2 gives the details of the larger run.

EXAMPLE 1

Bacterial alpha-amylase Concentrate Spray Dried
(Dryer has a water evaporation rate of 343 lbs./hour operating at 420° F./200° F. inlet/outlet temperature A strain of *Bacillus subtilis* selected to produce alpha amylase was grown on 24,000 pounds of medium containing cornstarch, corn steep water and inorganic salts using deep tank conditions to produce a culture with 21% dry solids and having 19,500 starch liquefying units (FM) per gram[1]. After filtration and washing on a rotary vacuum filter, 30,800 pounds of filtrate were obtained having 12,800 FM units per g and a solids content of 13.1%. Activity recovery was 85% with a reduction in solids from 5,000 lbs. to 4,035 lbs. The culture filtrate was concentrated by ultrafiltration to an activity of 45,900 FM/g in a weight of 7,055 pounds at a solids content of 19.0%. Solids (primarily in the form of low molecular weight solubles) were reduced from 4,035 lbs. to 1,340 lbs.—about 27% of the solids in the original crude culture or 33% of that in the filtrate before concentration. Only 18% enzyme activity was lost.

[1] An enzyme with 1,000 starch liquifying units per g reduces the vicosity of 300× its weight of potato starch by 90% in 10 minutes at 70° C. and pH 6.7.

Insoluble solids in the form of 400 pounds of cornstarch (5%) and 525 pounds of tricalcium phosphate (7%) were added to the concentrate to give a total weight of 8080 pounds at an activity of 39,900 FM/g. The concentrate plus additives was spray dried using a 160 mm wheel for atomization rotating at 18,700 RPM. Inlet temperature was set at 310° F. and the outlet temperature was set at 170° F. Product in the amount of 1889 pounds at an activity of 146,000 FM/g was collected plus 40 pounds of drying chamber dustings at 146,000 FM/g. Solids recovery was 94.6% in the product plus 2.0% in the dustings. Activity recovery was 85.3% in the product plus 1.8% in the dustings. The moisture content in the light colored free-flowing product was 5.26%. The dry concentrate has retained full activity and good flow character after storage for several months at room temperature.

EXAMPLE 2

Bacterial alpha-amylase concentrate Spray Dried
(Dryer has a water evaporation rate of 1,400 lbs. per hour operating at 420° F./200° F. inlet/outlet temperatures)

A strain of *Bacillus subtilis* selected to produce alpha amylase was grown under deep tank conditions on 31,400 pounds of medium containing cornstarch, corn steep water and inorganic salts to produce a culture containing 21% total solids and 16,500 FM per g. After filtration and washing, 40,900 pounds of filtrate at an activity of 10,360 FM/g. and a solids content of 13% were obtained. Activity recovery was 82% while solids were reduced from 6,594 pounds to 5,317 pounds. The culture filtrate was concentrated by ultrafiltration at 10° C. to a final weight of 8,600 pounds having a solids content of 15.4% and 43,300 FM. Solids, primarily in the form of highly colored, gummy, low molecular weight material were reduced from 5,317 pounds to 1,315 pounds. The discarded soluble solids of 4,002 pounds reduced the soluble solids in the concentrate by 75% with a loss in activity of only 12%.

Insoluble solids in the form of 450 pounds of cornstarch (5.6%) and 300 pounds of tricalcium phosphate (4.0%) were added to the concentrate to give 9,350 pounds of concentrate plus additives at 38,000 FM/g. The 9,350 pounds of mixture were spray dried using a 260 mm radial wheel rotating at 11,000 RPM for atomization. Inlet temperature was set at 315° F. and outlet temperature was 155° F. Product in the amount of 1,975 pounds at an activity of 170,000 FM/g was recovered. The activity recovery was 94.5% and the solids recovery was 99.6%. The light colored free flowing powder contained 4.0% moisture and remained free flowing when stored at room temperature for several months.

EXAMPLE 3

Neutral Fungal Protease Concentrate

This enzyme is prepared by growing a selected strain of *Aspergillus flavus-oryzae* on a medium containing a mixture of liver and soybean meals and ammonium phosphate under deep tank conditions to produce a fungal protease which can be used for protein modification, e.g. meat tenderization. Fungal mycelium and medium debris are removed from the crude culture by filtration on a rotary vacuum filter using diatomaceous earth as a filter aid. Proteolytic activity is measured as casein solubilization units (EE)[1]. The filtered cell free solution containing enzyme is concentrated by ultrafiltration and spray dried to give a dry stable free flowing solid of high activity as described below.

[1] Casein solubilization units (EE) are defined as follows: An enzyme with an activity of 1000 EE solubilizes nine times its weight of casein in 1 hour at 40° C. and pH 8.0.

The crude enzyme concentrate, 15,000 lbs., containing a total dry solids of 12.8% and 1,590 EE was filtered and washed on a rotary vacuum filter to give 18,480 lbs. of filtrate plus wash at 1,300 EE. Filtrate plus wash in the amount of 3,450 lbs. (equivalent to 2,800 lbs. of culture and 358 lbs. solids) was then concentrated to 440 lbs. at 9,250 EE and containing 12.3% solids in an ultrafiltration unit operating at 10° C. ±1° C. The total solids were reduced to 54 lbs. or 15% of the starting culture solids. The concentrate at 9,250 EE which contained about 90% of the activity present in 2,800 lbs. of culture was divided into two parts of 120 lbs. and 320 lbs. The second part was supplemented with 21 pounds of cornstarch and 24 pounds of calcium acetate added in sequence. Good mixing was employed to permit formation of finely divided water insoluble calcium phosphate intimately mixed with the starch. A total of 365 lbs. of supplemented concentrate was obtained. Activity recovery in the supplemented concentrate was 87.5% of that expected. The unsupplemented part 1 (120 lbs.) and supplemented part 2 (365 lbs. after addition) were then spray dried in the same drier separately using the same drying conditions: viz. 310° F./175° F. inlet and outlet air temperatures and atomized at 18,700 RPM with 160 mm wheel. Table IV gives the results obtained in this experiment.

TABLE IV

Spray Dried Neutral Fungal Protease

|  | Concentrate without Supplementation | Concentrate with Supplementation |
|---|---|---|
| Dry Solids | 12.3% | 23.0% |
| Activity before spray drying | 9,250 EE | 7,100 EE |
| Pounds Concentrate dried | 119 | 365 |
| Pounds of spray dry material produced Collected from |  |  |
| Cyclone | 9.5 | 79 |
| Chamber sweepings | 2.5 | 4 |
| Activity | 72,500 EE | 28,500 EE |
| Recovery of solids | 82% | 99% |
| Recovery of Activity | 79% | 91% |
| Moisture in Product | 6.54% | 6.79% |
| Product Physical Appearance | Dark Color Forms lumps on storage | Light in Color Free flowing character retained on storage |

EXAMPLE 4

Fungal Acid Protease Concentrate

This enzyme is produced by growth of a selected strain of *Aspergillus oryzae* under deep tank conditions on a medium containing a mixture of liver, soybean, and blood meals. The fungus produces a protease active on hemoglobin at pH 4.7 and other proteins which may be measured by its action on hemoglobin at pH 4.7 in terms of HU activity[1]. The protease is well suited for the modification of gluten in bakery operations.

For example, 106,000 lbs. of crude culture at 5850 HU and 12.6% total solids were filtered and water washed on a rotary vacuum filter to remove fungal mycelium and culture debris. Diatomaceous earth was used as a filter aid. The clear filtrate plus wash at 129,850 lbs. had an activity of 4,774 HU.

[1] An enzyme has an activity of 1,000 HU per g if 11.18 mg of it produces an increase in soluble nitrogen of 5.0 mg from 0.417 g hemoglobin in 5 hours at 40° C. and pH 4.7.

The culture filtrate plus wash was concentrated to 9,765 lbs. with an activity of 67,000 HU and a solids content of 18.1%. Activity recovery in the concentrate was about 90% of that in the crude culture but the total solids in the concentrate were reduced to 13.2% of that originally present in the culture.

The 9,756 lbs. of concentrate was supplemented with 60 lbs. of cornstarch and 60 lbs. of tricalcium phosphate added sequentially to give 9,885 lbs. of supplemented concentrate at 68290 HU and 20.94% solids. The mixture was spray dried at 330° F./175° F. inlet/outlet temperature with a radial atomizer of 260 mm rotating at 11,000 RPM to give 1,765 lbs. of free flowing light tan powder at 314,600 HU. The moisture level in the final product was 3.67%. Activity and solids recovery were 82% and 85% respectively.

Another lot of this enzyme Concentrate prepared from a different batch but processed in the same way was spray dried under the same conditions without any supplemental additives. The spray dried product was darker in color and exhibited very poor flow properties as compared to the above example with additives. Recovery of activity and solids were very satisfactory however, e.g. activity and solids recovery were 98% and 99% respectively.

The spray dried product produced from concentrate without supplements required the addition of flow aids to prepare a useable product. Preparation of a useable product after storage of the spray dried material prepared from unsupplemented concentrate required both grinding and addition of flow aids. Loss in activity and solids accompanied these operations. Caking and lumping of the spray dried material prepared without additives occurred during storage for several months.

EXAMPLE 5

Neutral Bacterial Protease Concentrate

This enzyme is prepared by growing a selected strain of *Bacillus subtilis* on a medium containing hominy, cornstarch and soybean meal under deep tank conditions to produce neutral bacterial protease. Activity is measured in terms of casein solubilization units (EE). The crude culture is filtered and washed using a rotary vacuum filter. The filtrate is concentrated by ultrafiltration and the concentrate is spray dried as described below.

The crude culture, 113,000 pounds, containing neutral bacterial protease with a solids content of 12.8% and an activity of 1,330 EE was filtered and washed on a rotary vacuum filter to give 137,000 pounds of filtrate plus wash at 950 EE. Filtrate in the amount of 5,800 pounds (eqivalent to the use of 4,785 pounds of culture and 612 pounds of dry solids) was concentrated at 10° C.±1° C. in an ultrafilter unit to 867 pounds of concentrate containing 11.2% solids and an activity of 6030 EE. The dry solids in the ultrafilter concentrate (867 lbs.) amounted to 97 pounds equivalent to about 16% of the solids present in the starting culture medium.

One part of the concentrate (450 lbs.) was spray dried without any additives while the second part (417 lbs.) was treated with a mixture of 13.9 pounds of cornstarch and 10.2 pounds of calcium phosphate added sequentially. The two parts of concentrate were spray dried separately in the same drier under the same conditions namely, 310° F./170° F. inlet/outlet air temperatures, atomized by centrifugal wheel of 160 mm turning at 18700 RPM. Table V below gives the results obtained from this experiment.

TABLE V

|  | Concentrate without Supplementation | Concentrate with Supplementation |
|---|---|---|
| Dry solids | 11.2% | 16.0% |
| Activity | 6030 EE | 5620 EE |
| Pounds liquid concentrate dried | 450 | 441 |
| Pounds Spray dry Product | 40.0 | 54 |
| Chamber Sweepings | 2.5 | 10 |
| Activity Product | 49600 EE | Product 28700 EE |
| Sweepings | 49600 EE | Sweepings 30100 EE |
| Recovery solids Product + Sweepings | 84% | 90.7% |
| Activity recovery Product + Sweepings | 77.7% | 74.7% |
| Physical Appearance of Spray Dried Product | Light Color Good flow Became lumpy on storage in sealed container Moisture = 5.07 | Light Color Good flow Retains good flow property on storage = 4.78 |

As noted this culture concentrate could be spray dried either with or without supplementation but the product caked up under storage unless the supplements were present at the time of spray drying. Addition of supplements after drying can be accomplished but in this case an added step of mixing is required and this must be accomplished before the spray dried material has caked. If caking occurs a grinding step is also necessary.

I claim:
1. A process for the preparation of a spray-dried enzyme composition which comprises: concentrating a liquid enzyme solution by ultrafiltration; adding to said concentrate water-insoluble salts, optionally in presence of water, insoluble suspenders and thickeners, intimately mixing the concentrate composition, and spray-drying the concentrate composition at air inlet temperatures from about 150° C. to about 180° C. and air outlet temperatures from about 65° C. to about 90° C.

2. A process according to claim 1 wherein the water insoluble salts are selected from the group consisting of tribasic calcium phosphate, tribasic magnesium phosphate, calcium carbonate, calcium hypophosphate, calcium magnesium silicate, calcium silicate, calcium sulfite, calcium tartarate, magnesium oxide and magnesium silicate.

3. A process according to claim 2 wherein the water insoluble salt is tribasic calcium phosphate.

4. A process according to claim 3 wherein the water insoluble salt is formed in situ by the reaction of a water soluble phosphate salt and a water soluble or insoluble calcium salt.

5. A process according to claim 4 wherein the liquid enzyme solution is obtained from a submerged culture.

6. A process according to claim 5 wherein the water soluble phosphate salt is selected from the group consisting of sodium potassium and ammonium phosphates or mixtures thereof and the calcium salt is selected from the group consisting of acetate, carbonate, chloride, hydroxide and sulfate or mixtures thereof.

7. A process according to claim 4 wherein suspenders and thickeners are added which are selected from the group consisting of cornstarch, tapioca, potatoe starch, and cellulose.

8. A process according to claim 6 wherein the enzyme is a protease derived from a Bacillus sps.

9. A process according to claim 6 wherein the enzyme is a protease derived from an Aspergillus sps.

10. A process according to claim 6 wherein the enzyme is an amylase derived from a Bacillus sps.

* * * * *